(12) United States Patent
Learmonth et al.

(10) Patent No.: US 8,975,410 B2
(45) Date of Patent: Mar. 10, 2015

(54) CRYSTAL FORMS OF 5-[3-(2,5-DICHLORO-4, 6-DIMETHYL-1-OXY-PYRIDINE-3-YL)[1,2,4] OXADIAZOL-5-YL]-3-NITROBENZENE-1,2-DIOL

(75) Inventors: David Alexander Learmonth, Alfena (PT); Keith Lorimer, West Lafayette, IN (US); Kevin Wayne Meyer, West Lafayette, IN (US); Tibor Eszenyi, Tiszalök (HU); Álmosné Kovách, Tiszavasvári (HU)

(73) Assignee: BIAL—Portela & CA., S.A. (PT)

( * ) Notice: Subject to any disclaimer, the term of this patent is extended or adjusted under 35 U.S.C. 154(b) by 418 days.

(21) Appl. No.: 12/933,044

(22) PCT Filed: Mar. 16, 2009

(86) PCT No.: PCT/PT2009/000013
§ 371 (c)(1),
(2), (4) Date: Dec. 2, 2010

(87) PCT Pub. No.: WO2009/116882
PCT Pub. Date: Sep. 24, 2009

(65) Prior Publication Data
US 2011/0112301 A1    May 12, 2011

Related U.S. Application Data

(60) Provisional application No. 61/069,721, filed on Mar. 17, 2008.

(51) Int. Cl.
*C07D 413/04* (2006.01)

(52) U.S. Cl.
CPC ................................... *C07D 413/04* (2013.01)
USPC ....................................................... 546/269.4

(58) Field of Classification Search
CPC .......................... C07D 413/04; A61K 31/4439
USPC ........................................ 546/269.4; 514/340
See application file for complete search history.

(56) References Cited

U.S. PATENT DOCUMENTS 6,627,646 B2 * 9/2003 Bakale et al. ................. 514/322

FOREIGN PATENT DOCUMENTS

WO    WO 2007/013830    2/2007
WO    WO 2008/094053    8/2008

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Doelker, english translation of S.T.P, Pratiques (1999), 9(5), 399-409, pp. 1033.*
Doelker, english translation of Ann. Pharm. Fr., 2002, 60: 161-176, pp. 1-39.*
Taday et al., "Using Terahertz, etc.," J of Pharm. Sci., 92(4), 2003, 831-838.*
Otuska et al., "Effect of Polymorphic, etc.," Chem. Pharm. Bull., 47(6) 852-856 (1999).*
Copy of International Preliminary Report on Patentability issued in PCT/PT2009/000013 dated Sep. 21, 2010.
International Search Report and Written Opinion for PCT Application No. PCT/PT2009/000013 dated Jun. 9, 2009.

* cited by examiner

*Primary Examiner* — Patricia L Morris
(74) *Attorney, Agent, or Firm* — The Marbury Law Group, PLLC (57) ABSTRACT

This invention relates to novel polymorphs of $(HO)_2NO_2(C_6H)—(C_2N_2O)—(C_5N)(CH_3)_2Cl_2O$, to processes for their preparation, and to pharmaceutical compositions containing said novel polymorphs as active pharmaceutical ingredient.

5 Claims, 6 Drawing Sheets

CRYSTAL FORMS OF 5-[3-(2,5-DICHLORO-4, 6-DIMETHYL-1-OXY-PYRIDINE-3-YL)[1,2,4] OXADIAZOL-5-YL]-3-NITROBENZENE-1,2-DIOL

RELATED APPLICATIONS

This application is the U.S. National Stage of PCT Application Number PCT/PT2009/000013, filed Mar. 16, 2009, which claims the benefit of priority of U.S. Provisional Application No. 61/069,721, filed Mar. 17, 2008. The contents of the foregoing applications are incorporated herein by reference.

TECHNICAL FIELD

This invention relates to novel polymorphs of 5-[3-(2,5-dichloro-4,6-dimethyl-1-oxy-pyridin-3-yl)-[1,2,4]oxadiazol-5-yl]-3-nitrobenzene-1,2-diol, an inhibitor of catechol-O-methyltransferase (COMT), to processes for their preparation, and to pharmaceutical compositions containing said novel polymorphs as active pharmaceutical ingredient.

BACKGROUND

Despite being used in clinical practice for several decades, levodopa (L-DOPA) continues to be the gold standard drug for the symptomatic treatment of Parkinson's disease. This has helped to maintain keen interest in the development of inhibitors of the enzyme catechol-O-methyltransferase (COMT) based on the hypothesis that inhibition of this enzyme may provide clinical improvements in patients afflicted by diseases such as Parkinson's disease and undergoing treatment with L-DOPA and a peripheral amino acid decarboxylase (AADC) inhibitor.

The rationale for the use of COMT inhibitors as adjuncts to L-DOPA/AADC therapy is based on their ability to reduce metabolic O-methylation of L-DOPA to 3-O-methyl-L-DOPA (3-OMD). The duration of L-DOPA induced clinical improvement is brief as a result of the short in vivo half-life of L-DOPA which contrasts with the long half-life of 3-OMD. Additionally, 3-OMD competes with L-DOPA for transport across the blood-brain barrier (BBB), which means that only a very limited amount of an orally administered dose of L-DOPA actually reaches the site of action, i.e. the brain. Commonly, within only a few years of starting L-DOPA therapy with the usual dosage regime, L-DOPA induced clinical improvement declines at the end of each dose cycle, giving rise to the so-called 'wearing-off' pattern of motor fluctuations. A close relationship between the 'wearing-off' phenomenon and accumulation of 3-OMD has been described (Tohgi, H., et al., Neurosci. Letters, 132:19-22, 1992). It has been speculated that this may result from impaired brain penetration of L-DOPA due to competition for the transport system across the BBB with 3-OMD (Reches, A. et al., Neurology, 32:887-888, 1982) or more simply that there is less L-DOPA available to reach the brain (Nutt, J. G., Fellman, J. H., Clin. Neuropharmacol., 7:35-49, 1984). In effect, COMT inhibition protects L-DOPA from metabolic breakdown in the periphery through O-methylation, such that with repeated doses of L-DOPA, the mean plasma L-DOPA concentration is raised. In addition to reduced competition for transport into the brain, a significantly greater percentage of the orally administered dose of L-DOPA is able to reach the site of action. Thus, COMT inhibition serves to increase the bioavailability of L-DOPA and therefore the duration of antiparkinsonian action is prolonged with single doses of L-DOPA (Nutt, J. G., Lancet, 351:1221-1222, 1998).

5-[3-(2,5-dichloro-4,6-dimethyl-1-oxy-pyridin-3-yl)-[1,2,4]oxadiazol-5-yl]-3-nitrobenzene-1,2-diol is a COMT inhibitor exhibiting an exceptionally long duration of action as well as balanced properties of bioactivity, bioavailability and safety. It markedly enhances the bioavailability of L-DOPA, increases the delivery of L-DOPA to the brain and significantly augments the levels of dopamine in the brain over extended periods of time.

As such, 5-[3-(2,5-dichloro-4,6-dimethyl-1-oxy-pyridin-3-yl)-[1,2,4]oxadiazol-5-yl]-3-nitrobenzene-1,2-diol is a promising candidate for treating a subject afflicted by a central or peripheral nervous system disorder, in particular for treating mood disorders, movement disorders such as Parkinson's disease and parkinsonian disorders and restless leg syndrome, gastrointestinal disturbances, oedema formation states and hypertension.

Methods of preparing 5-[3-(2,5-dichloro-4,6-dimethyl-1-oxy-pyridin-3-yl)-[1,2,4]oxadiazol-5-yl]-3-nitrobenzene-1,2-diol are described in WO2007/013830 A1.

The ability of a substance, for example 5-[3-(2,5-dichloro-4,6-dimethyl-1-oxy-pyridin-3-yl)-[1,2,4]oxadiazol-5-yl]-3-nitrobenzene-1,2-diol, to exist in more than one crystalline form is defined as polymorphism and these different crystalline forms may be referred to as "polymorphic modifications" or "polymorphs". For the purposes of this specification, the term 'polymorph' may also encompass pseudo-polymorphs. In general, polymorphism is caused by the ability of the molecule of a substance to change its conformation or to form different intermolecular and intramolecular interactions, particularly hydrogen bonds, resulting in different atomic arrangements in the crystal lattices of the different polymorphs. The polymorphs of a substance possess different crystal lattice energies and, thus, also exhibit different solid state physical properties such as morphology, density, melting point, colour, stability, dissolution rate, milling facility, granulation properties, compacting properties etc.

There are a number of processes for characterizing polymorphs. State of the art technologies include X-ray-based technologies such as X-ray powder diffraction, single crystal X-ray diffraction, microscopy, differential scanning calorimetry, and spectroscopic methods such as IR, near-IR (NIR), Raman and solid state NMR.

In pharmaceutical compositions, the use of different polymorphs often influences factors such as the preparation of pharmaceutical compositions, their stability, dissolution properties, bioavailability and, consequently, their action. In other words, the use of polymorphs allows modulation of the performance of an active pharmaceutical ingredient (API) such as 5-[3-(2,5-dichloro-4,6-dimethyl-1-oxy-pyridin-3-yl)-[1,2,4]oxa-diazol-5-yl]-3-nitrobenzene-1,2-diol as well as affecting the formulation of the API.

Accordingly, it is the object of the present invention to provide novel polymorphs of 5-[3-(2,5-dichloro-4,6-dimethyl-1-oxy-pyridin-3-yl)-[1,2,4]oxadiazol-5-yl]-3-nitrobenzene-1,2-diol.

DESCRIPTION

The present invention not only relates to the provision of novel polymorphs of 5-[3-(2,5-dichloro-4,6-dimethyl-1-oxy-pyridin-3-yl)-[1,2,4]oxadiazol-5-yl]-3-nitrobenzene-1,2-diol (henceforth referred to as "compound of the invention"), but also to processes for their preparation, and to pharmaceutical compositions containing one or more of said novel polymorphs as active ingredient.

Figure 1:
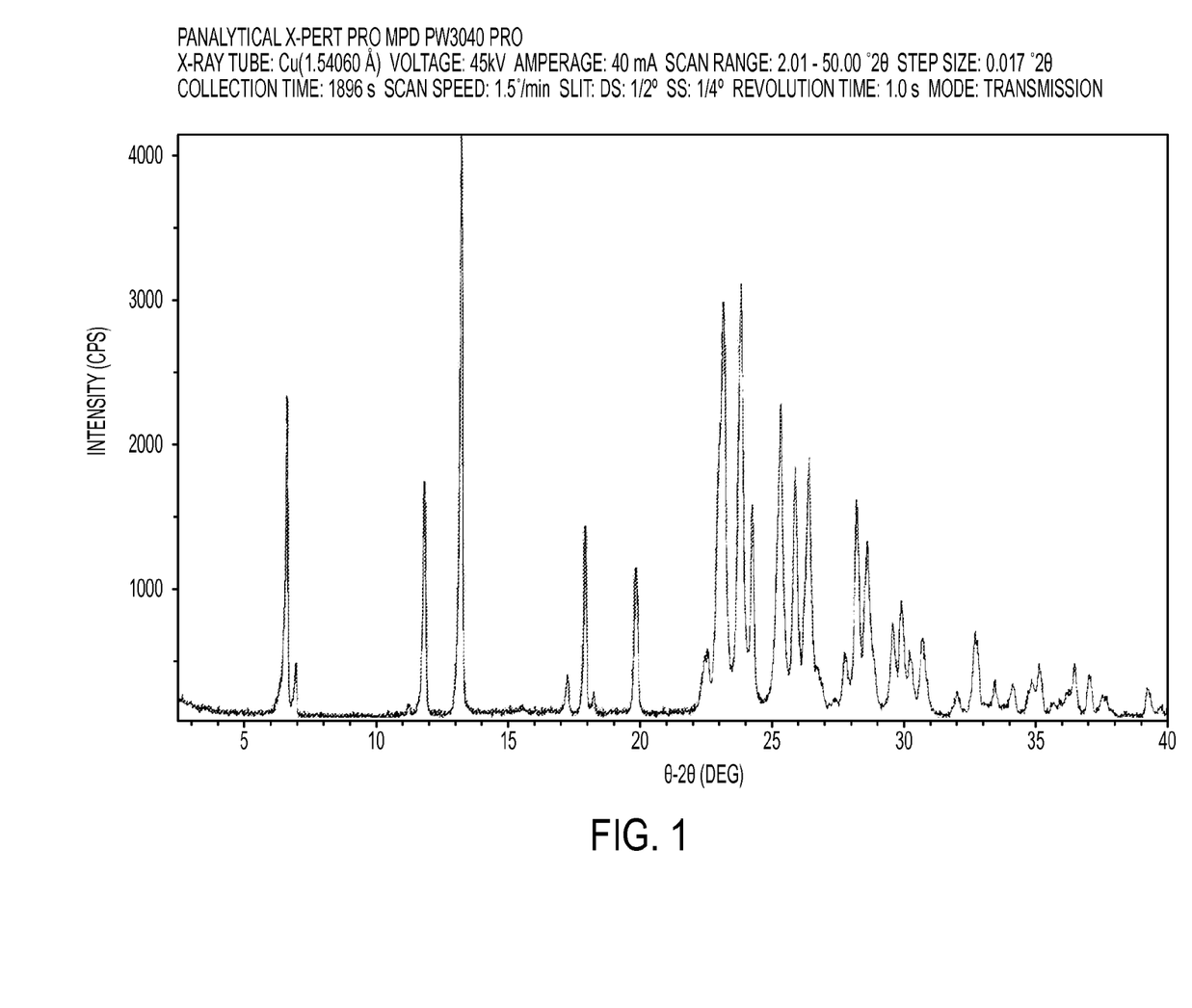
FIG. 1 is an exemplary XRPD pattern of Form A of 5-[3-(2,5-dichloro-4,6-dimethyl-1-oxy-pyridin-3-yl)-[1,2,4]oxadiazol-5-yl]-3-nitrobenzene-1,2-diol, according to one embodiment of the invention.

In one embodiment, the present invention relates to a polymorph of the compound of the invention which is, in the following specification, referred to as polymorph A. A process for the preparation of polymorph A is given in the experimental section. Polymorph A is a crystalline polymorph and, thus, characterizable by its powder X-ray diffraction pattern (XRPD). The diffraction pattern may either be experimentally recorded or calculated from the results of the measurement of the unit cell parameters of the polymorph. In the following, characteristic peaks of the XRPDs of the polymorphs of the invention are given in degrees $2\theta$ (Cu-K$\alpha$ radiation).

Polymorph A is characterizable by one or more of the peaks given in the following table.

TABLE 1

| XRPD of polymorph A | |
|---|---|
| Peak Position (°2θ) | Rel. Intensity (%) |
| 6.6 | 55 |
| 6.9 | 9 |
| 11.8 | 40 |
| 13.2 | 100 |
| 17.2 | 8 |
| 17.9 | 33 |
| 19.8 | 25 |
| 22.6 | 12 |
| 23.2 | 71 |
| 23.8 | 74 |
| 24.3 | 36 |
| 25.3 | 53 |
| 25.9 | 42 |
| 26.4 | 45 |
| 27.8 | 11 |
| 28.2 | 36 |
| 28.6 | 29 |
| 29.6 | 16 |
| 29.9 | 20 |
| 30.3 | 11 |
| 30.7 | 14 |
| 32.0 | 5 |
| 32.7 | 14 |
| 33.5 | 6 |
| 34.1 | 6 |
| 35.1 | 9 |
| 36.5 | 9 |
| 37.0 | 8 |
| 37.6 | 4 |
| 39.2 | 5 |

Preferably, polymorph A is characterized by one or more of the above peaks in the range of from about 5 to about 25°/2θ which is a highly characteristic region of XRPDs. More preferably, polymorph A is characterized by 2 to 10, preferably 3 to 5, peaks within the range of from about 5 to about 25°/2θ. Even more preferably, the polymorph A is characterized by the signals at 6.6, 13.2, 17.9, 23.2, 23.8 and 24.3°/2θ. Most preferably, polymorph A is characterized by the signals at 6.6, 13.2, 17.9 and 23.8°/2θ.

One skilled in the art will recognize that the 2θ degrees given above will generally be reproducible to within a range from about ±0.10 2θ degrees to about ±0.20 2θ degrees, with a preferred range being ±0.10 2θ degrees. See e.g. United States Pharmacopoeia XXV (2002), p. 2088-2089. This also applies to other XRPD data given in this specification.

In addition, polymorph A may also be characterizable by having an exotherm at 251° C. in a Differential Scanning calorimetry (DSC) thermogram.

One skilled in the art will recognize that the exotherm given above will generally be reproducible to within a range from about ±0.5 to 3° C., preferably ±2° C., more preferably ±1° C., and most preferably ±0.5° C. This also applies to other DSC and also the melt-onset of hot stage data given in this specification.

Hotstage analysis also indicates that polymorph A may also be characterised by exhibiting a melt onset at 238° C.

Furthermore, polymorph A may also be characterized by being non-hygroscopic over the range of about 5% to about 95%, more preferably from about 25% to about 80%, and even more preferably from about 40% to about 60%, relative humidity at 25° C. over a period of 3 months.

In addition, polymorph A is preferably an anhydrate as is evidenced by a lack of solvent desorption in combined Differential Scanning calorimetry (DSC) and Thermogravimetric Analysis (TGA) experiments prior to energetic decomposition.

Polymorph A is also characterizable by one or more of the following FT-Raman Peak Positions:

TABLE 2

| Raman spectra of polymorph A | |
|---|---|
| Peak position (cm$^{-1}$) | Rel. Intensity (%) |
| 145 | 35 |
| 170 | 22 |
| 216 | 22 |
| 237 | 16 |
| 256 | 23 |
| 285 | 14 |
| 339 | 27 |
| 370 | 24 |
| 420 | 14 |
| 442 | 12 |
| 465 | 14 |

TABLE 2-continued

Raman spectra of polymorph A

| Peak position (cm$^{-1}$) | Rel. Intensity (%) |
|---|---|
| 505 | 37 |
| 526 | 19 |
| 710 | 11 |
| 810 | 43 |
| 974 | 10 |
| 1007 | 14 |
| 1059 | 16 |
| 1159 | 40 |
| 1228 | 38 |
| 1254 | 23 |
| 1277 | 23 |
| 1325 | 44 |
| 1387 | 30 |
| 1414 | 32 |
| 1448 | 25 |
| 1498 | 23 |
| 1537 | 63 |
| 1589 | 100 |
| 1628 | 50 |
| 2927 | 17 |

Preferably, polymorph A is characterizable by one or more, preferably 2 to 6, and more preferably 3 to 5, peak positions in the above table. More preferably, polymorph A is characterized by one or more of the peaks at 145, 505, 810, 1159, 1228, 1325, 1537, 1589, and 1628 cm$^{-1}$. Most preferably, polymorph A is characterized by the peaks at 810, 1325, 1537, 1589, and 1628 cm$^{-1}$.

One skilled in the art will recognize that the FT-Raman Peak Positions will generally be reproducible within a range from about ±0 cm$^{-1}$ to ±5 cm$^{-1}$, preferably from ±1 cm$^{-1}$ to ±3 cm$^{-1}$, most preferably ±2 cm$^{-1}$. This also applies to the other Raman data presented in this specification.

Polymorph A is also characterizable by one or more of the following peak positions in Solid State $^{13}$C-NMR:

TABLE 3

Solid State 13C-NMR of polymorph A
Peak position
(ppm)

| |
|---|
| 174.0 |
| 163.9 |
| 150.4 |
| 148.8 |
| 144.5 |
| 140.2 |
| 134.8 |
| 133.2 |
| 129.8 |
| 124.9 |
| 124.0 |
| 122.1 |
| 114.6 |
| 22.5 |
| 15.7 |

Preferably, polymorph A is characterizable by one or more, preferably 2 to 6, and more preferably 3 to 5, peak positions in the above table. Most preferably, polymorph A is characterized by the peaks at 15.7, 114.6, 148.8 and 174.0 ppm.

One skilled in the art will recognize that the $^{13}$C-ssNMR peaks will generally be reproducible within a range from about ±0.1 ppm to ±0.3 ppm, preferably ±0.2 ppm. This also applies to the other NMR data presented in this specification.

In another embodiment, the present invention relates to a polymorph of the compound of the invention which is, in the following specification, referred to as polymorph B. A process for the preparation of polymorph B is given in the experimental section.

Figure 2:
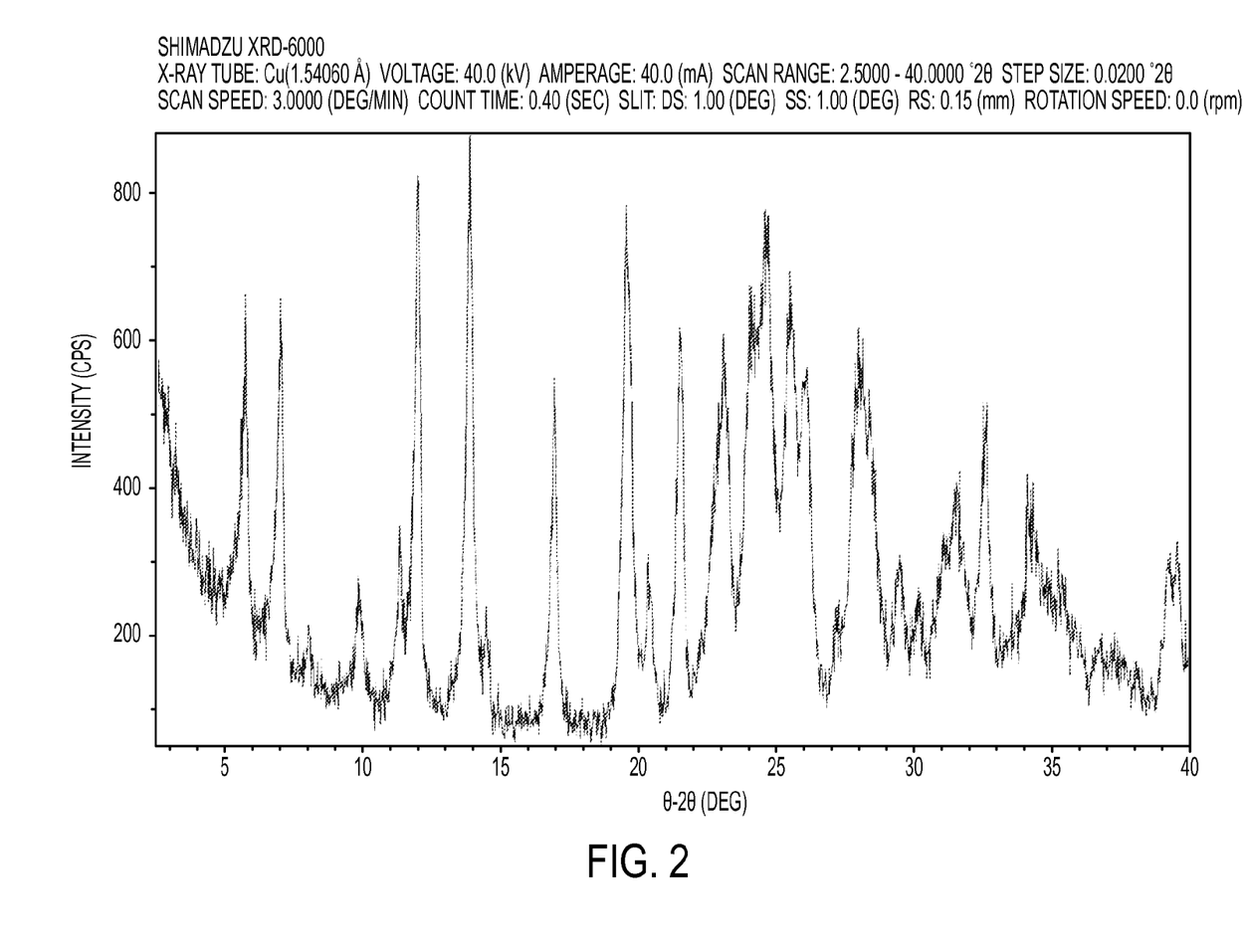
FIG. 2 is an exemplary XRPD pattern of Form B of 5-[3-(2,5-dichloro-4,6-dimethyl-1-oxy-pyridin-3-yl)-[1,2,4]oxadiazol-5-yl]-3-nitrobenzene-1,2-diol, according to one embodiment of the invention.

Polymorph B is a crystalline polymorph and, thus, characterizable by its powder X-ray diffraction pattern (XRPD). The diffraction pattern was recorded with Cu-Kα radiation and is characterizable by one or more of the peaks given in the following table.

TABLE 4

XRPD of polymorph B

| Peak Position (°2θ) | Rel. Intensity (%) |
|---|---|
| 5.7 | 69 |
| 6.9 | 68 |
| 8.0 | 24 |
| 9.8 | 26 |
| 11.3 | 36 |
| 11.9 | 93 |
| 13.8 | 100 |
| 14.4 | 27 |
| 16.9 | 63 |
| 19.6 | 87 |
| 20.4 | 28 |

Preferably, polymorph B is characterized by one or more of the above peaks in the range of from about 5 to about 25°/2θ which is a highly characteristic region of XRPDs. More preferably, polymorph B is characterized by 2 to 10, preferably 3 to 5, peaks within the range of from about 5 to about 25°/2θ. Even more preferably, the polymorph B is characterized by the signals at 5.7, 6.9, 11.9, 13.8, 16.9 and 19.6°/2θ. Most preferably, polymorph B is characterized by the signals at 5.7, 6.9, 13.8 and 19.6°/2θ.

In addition, polymorph B may also be characterizable by having an exotherm at 237° C. in a Differential Scanning calorimetry (DSC) thermogram. Such analyses may also indicate a shoulder peak at 231° C.

In addition, polymorph B is preferably an anhydrate as is evidenced by a lack of solvent desorption in combined Differential Scanning calorimetry (DSC) and Thermogravimetric Analysis (TGA) experiments prior to energetic decomposition. However, molecular packaging of polymorph B allows the accommodation of crystal water without substantially altering the crystal lattice.

Polymorph B is also characterizable by one or more of the following FT-Raman Peak Positions:

TABLE 5

Raman spectra of polymorph B

| Peak position (cm$^{-1}$) | Rel. Intensity (%) |
|---|---|
| 141 | 26 |
| 214 | 23 |
| 235 | 16 |
| 253 | 20 |
| 280 | 14 |
| 339 | 25 |
| 361 | 18 |
| 372 | 19 |
| 399 | 15 |
| 415 | 18 |
| 440 | 12 |
| 463 | 15 |
| 505 | 49 |
| 526 | 21 |
| 710 | 14 |

TABLE 5-continued

Raman spectra of polymorph B

| Peak position (cm$^{-1}$) | Rel. Intensity (%) |
|---|---|
| 812 | 54 |
| 887 | 11 |
| 926 | 13 |
| 970 | 12 |
| 1001 | 22 |
| 1059 | 19 |
| 1157 | 10 |
| 1227 | 14 |
| 1292 | 49 |
| 1317 | 43 |
| 1385 | 50 |
| 1406 | 34 |
| 1444 | 32 |
| 1504 | 27 |
| 1537 | 44 |
| 1583 | 100 |
| 1630 | 69 |
| 2933 | 31 |

Preferably, polymorph B is characterizable by one or more, preferably 2 to 6, and more preferably 3 to 5, peak positions in the above table. More preferably, polymorph B is characterized by one or more of the peaks at 505, 1292, 1317, 1385, 1537, 1583, and 1630 cm$^{-1}$. Most preferably, polymorph B is characterized by the peaks at 505, 1292, 1385, 1583, and 1630 cm$^{-1}$.

Polymorph B is also characterizable by one or more of the following peak positions in Solid State $^{13}$C-NMR:

TABLE 6

| Solid State 13C-NMR of polymorph B Peak positions (ppm) |
|---|
| 174.4 |
| 164.7 |
| 150.3 |
| 139.1 |
| 133.9 |
| 132.8 |
| 123.5 |
| 120.3 |
| 114.0 |
| 112.6 |
| 19.8 |
| 16.6 |

Preferably, polymorph B is characterizable by one or more, preferably 2 to 6, and more preferably 3 to 5, peak positions in the above table. Most preferably, polymorph B is characterized by the peaks at 150.3, 133.9, 112.6 and 19.8 ppm.

In yet another embodiment, the present invention relates to a polymorph of the compound of the invention which is, in the following specification, referred to as polymorph C. A process for the preparation of polymorph C is given in the experimental section.

Figure 3:
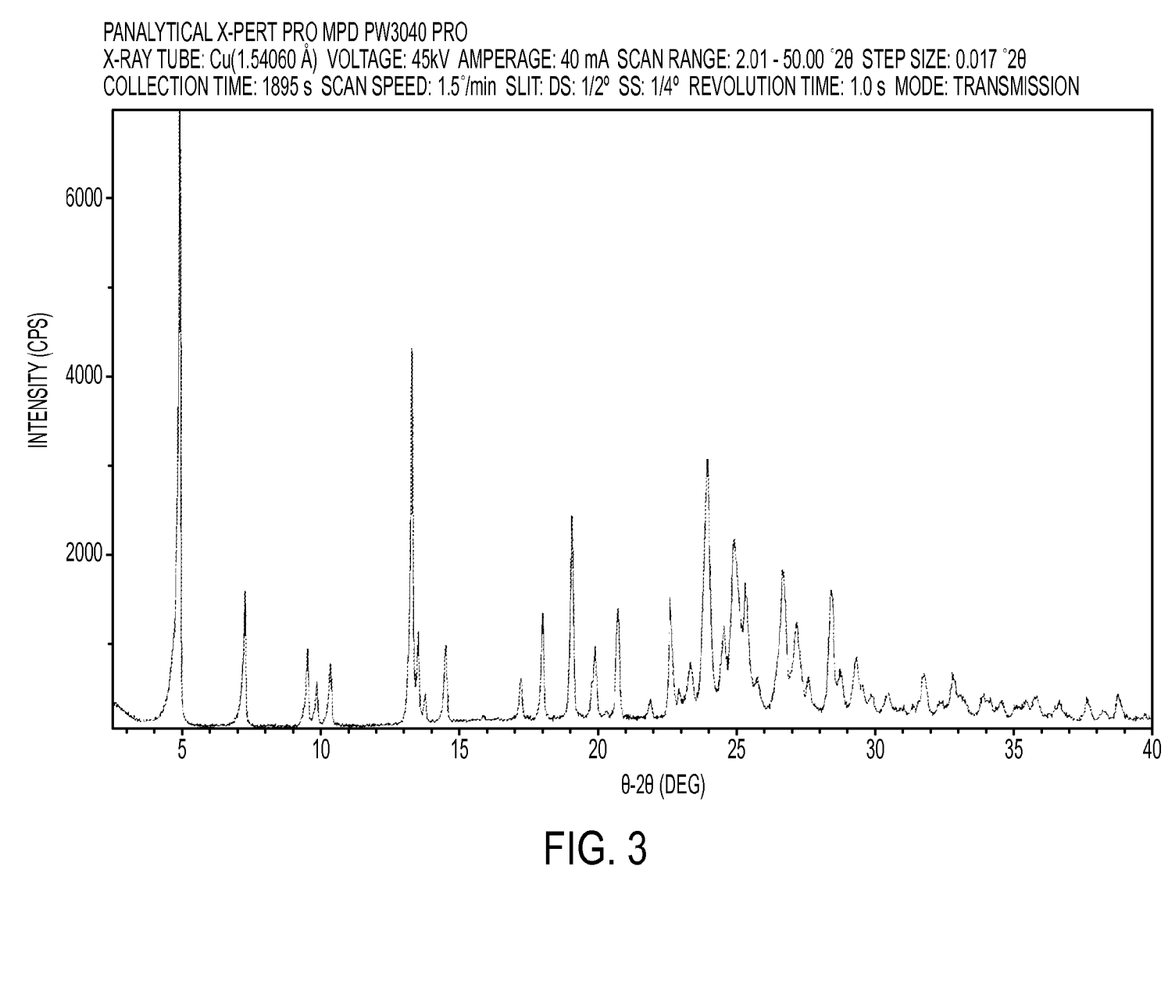
FIG. 3 is an exemplary XRPD pattern of Form C of 5-[3-(2,5-dichloro-4,6-dimethyl-1-oxy-pyridin-3-yl)-[1,2,4]oxadiazol-5-yl]-3-nitrobenzene-1,2-diol, according to one embodiment of the invention.

Polymorph C is a crystalline polymorph and, thus, characterizable by one or more of the peaks of its powder X-ray diffraction pattern (XRPD). The diffraction pattern was recorded with Cu-Kα radiation and is given in the following table.

TABLE 7

| Peak Position (°2θ) | Rel. Intensity (%) |
|---|---|
| 4.9 | 100 |
| 7.3 | 22 |
| 9.5 | 13 |
| 9.9 | 8 |
| 10.3 | 10 |
| 13.3 | 61 |
| 13.8 | 6 |
| 14.5 | 13 |
| 17.2 | 8 |
| 18.0 | 19 |
| 19.1 | 34 |
| 19.9 | 13 |
| 20.7 | 19 |
| 21.9 | 5 |
| 22.6 | 21 |
| 23.4 | 11 |
| 24.0 | 44 |
| 24.6 | 16 |
| 24.9 | 31 |
| 25.3 | 24 |
| 25.8 | 8 |
| 26.7 | 25 |
| 27.2 | 16 |
| 27.6 | 8 |
| 28.4 | 23 |
| 28.8 | 9 |
| 29.3 | 11 |
| 29.9 | 5 |
| 30.5 | 5 |
| 31.8 | 8 |
| 32.8 | 8 |
| 33.9 | 6 |
| 34.6 | 5 |
| 35.4 | 5 |
| 35.8 | 5 |
| 36.6 | 5 |
| 37.6 | 5 |
| 38.2 | 3 |
| 38.7 | 6 |

Preferably, polymorph C is characterized by one or more of the above peaks in the range of from about 5 to about 25°/2θ which is a highly characteristic region of XRPDs. More preferably, polymorph C is characterized by 2 to 10, preferably 3 to 5, peaks within the range of from about 5 to about 25°/2θ. Even more preferably, the polymorph C is characterized by the signals at 4.9, 7.3, 13.3, 19.1, 21.9, 23.4 and 24.0°/2θ. Most preferably, polymorph C is characterized by the signals at 4.9, 13.3, 19.1 and 24.0°/2θ.

Polymorph C may also be characterised by showing an exotherm at 203° C. in a Differential Scanning calorimetry (DSC) thermogram.

Polymorph C is also characterizable by one or more of the following FT-Raman Peak Positions:

TABLE 8

| Raman spectra of polymorph C | |
|---|---|
| Peak position (cm$^{-1}$) | Rel. Intensity (%) |
| 143 | 38 |
| 214 | 19 |
| 237 | 14 |
| 253 | 17 |
| 282 | 14 |
| 299 | 13 |
| 339 | 30 |
| 370 | 20 |

TABLE 8-continued

Raman spectra of polymorph C

| Peak position (cm$^{-1}$) | Rel. Intensity (%) |
| --- | --- |
| 401 | 13 |
| 418 | 14 |
| 444 | 10 |
| 465 | 12 |
| 507 | 40 |
| 530 | 15 |
| 667 | 13 |
| 710 | 14 |
| 739 | 11 |
| 810 | 41 |
| 972 | 11 |
| 1003 | 14 |
| 1061 | 20 |
| 1147 | 21 |
| 1244 | 42 |
| 1281 | 34 |
| 1317 | 36 |
| 1352 | 36 |
| 1387 | 55 |
| 1406 | 45 |
| 1450 | 30 |
| 1483 | 22 |
| 1506 | 24 |
| 1537 | 42 |
| 1585 | 100 |
| 1630 | 59 |
| 2918 | 15 |

Preferably, polymorph C is characterizable by one or more, preferably 2 to 6, and more preferably 3 to 5, peak positions in the above table. More preferably, polymorph C is characterized by one or more of the peaks at 143, 507, 810, 1244, 1281, 1317, 1352, 1387, 1406, 1537, 1585, and 1630 cm$^{-1}$. Most preferably, polymorph C is characterized by the peaks at 1387, 1406, 1537, 1585, and 1630 cm$^{-1}$.

Polymorph C is also characterizable by one or more of the following peak positions in Solid State $^{13}$C-ssNMR:

TABLE 9

Solid State 13C-NMR of polymorph C
Peak positions (ppm)

| |
| --- |
| 173.9 |
| 165.0 |
| 150.7 |
| 141.0 |
| 138.6 |
| 133.5 |
| 122.8 |
| 120.3 |
| 114.0 |
| 112.4 |
| 41.1 |
| 20.2 |
| 17.9 |

Preferably, polymorph C is characterizable by one or more, preferably 2 to 6, and more preferably 3 to 5, peak positions in the above table. Most preferably, polymorph C is characterized by the peaks at 150.7, 133.5, 114.0 and 20.2 ppm.

In yet another embodiment, the present invention relates to a polymorph of the compound of the invention which is, in the following specification, referred to as polymorph D. A process for the preparation of polymorph D is given in the experimental section.

Figure 4:
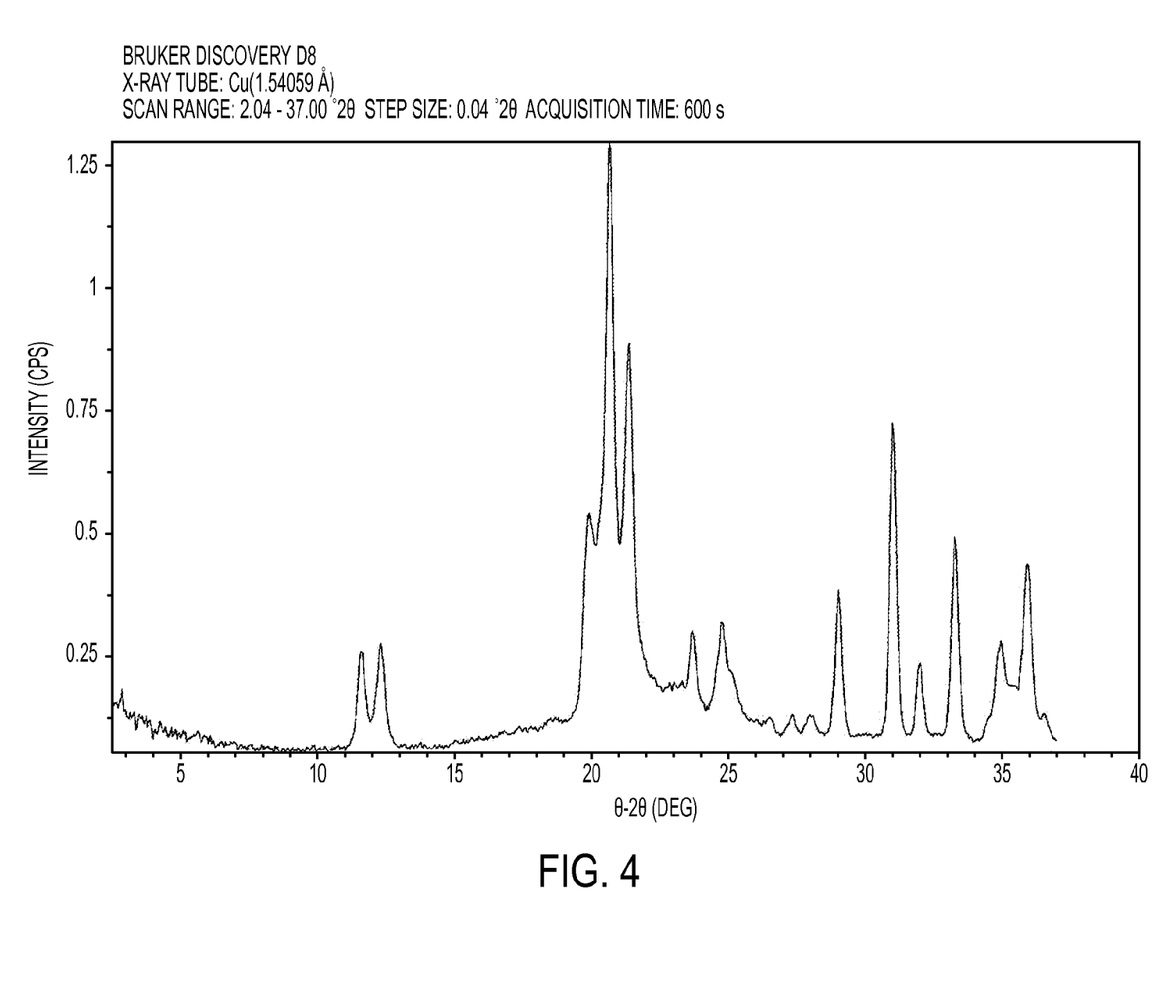
FIG. 4 is an exemplary XRPD pattern of Form D of 5-[3-(2,5-dichloro-4,6-dimethyl-1-oxy-pyridin-3-yl)-[1,2,4]oxadiazol-5-yl]-3-nitrobenzene-1,2-diol, according to one embodiment of the invention.

Polymorph D is a crystalline polymorph and, thus, characterizable by one or more of the peaks of its powder X-ray diffraction pattern (XRPD). The diffraction pattern was recorded with Cu-Kα radiation and is given in the following table.

TABLE 10

XRPD of polymorph D

| Peak Position (°2θ) | Rel. Intensity (%) |
| --- | --- |
| 11.6 | 21 |
| 12.3 | 23 |
| 20.0 | 43 |
| 20.7 | 100 |
| 21.4 | 69 |
| 23.8 | 25 |
| 24.8 | 26 |
| 26.6 | 11 |
| 27.4 | 12 |
| 28.0 | 12 |
| 29.1 | 31 |
| 31.1 | 56 |
| 32.0 | 20 |
| 33.3 | 39 |
| 35.0 | 23 |
| 36.0 | 35 |

Preferably, polymorph D is characterized by one or more of the above peaks in the range of from about 5 to about 25°/2θ which is a highly characteristic region of XRPDs. More preferably, polymorph D is characterized by 2 to 10, preferably 3 to 5, peaks within the range of from about 5 to about 25°/2θ. Even more preferably, the polymorph D is characterized by the signals at 11.6, 12.3, 20.0, 20.7, 21.4 and 24.8°/2θ. Most preferably, polymorph D is characterized by the signals at 12.3, 20.0, 20.7 and 21.4°/2θ.

In yet another embodiment, the present invention relates to a polymorph of the compound of the invention which is, in the following specification, referred to as polymorph E. A process for the preparation of polymorph E is given in the experimental section.

Figure 5:
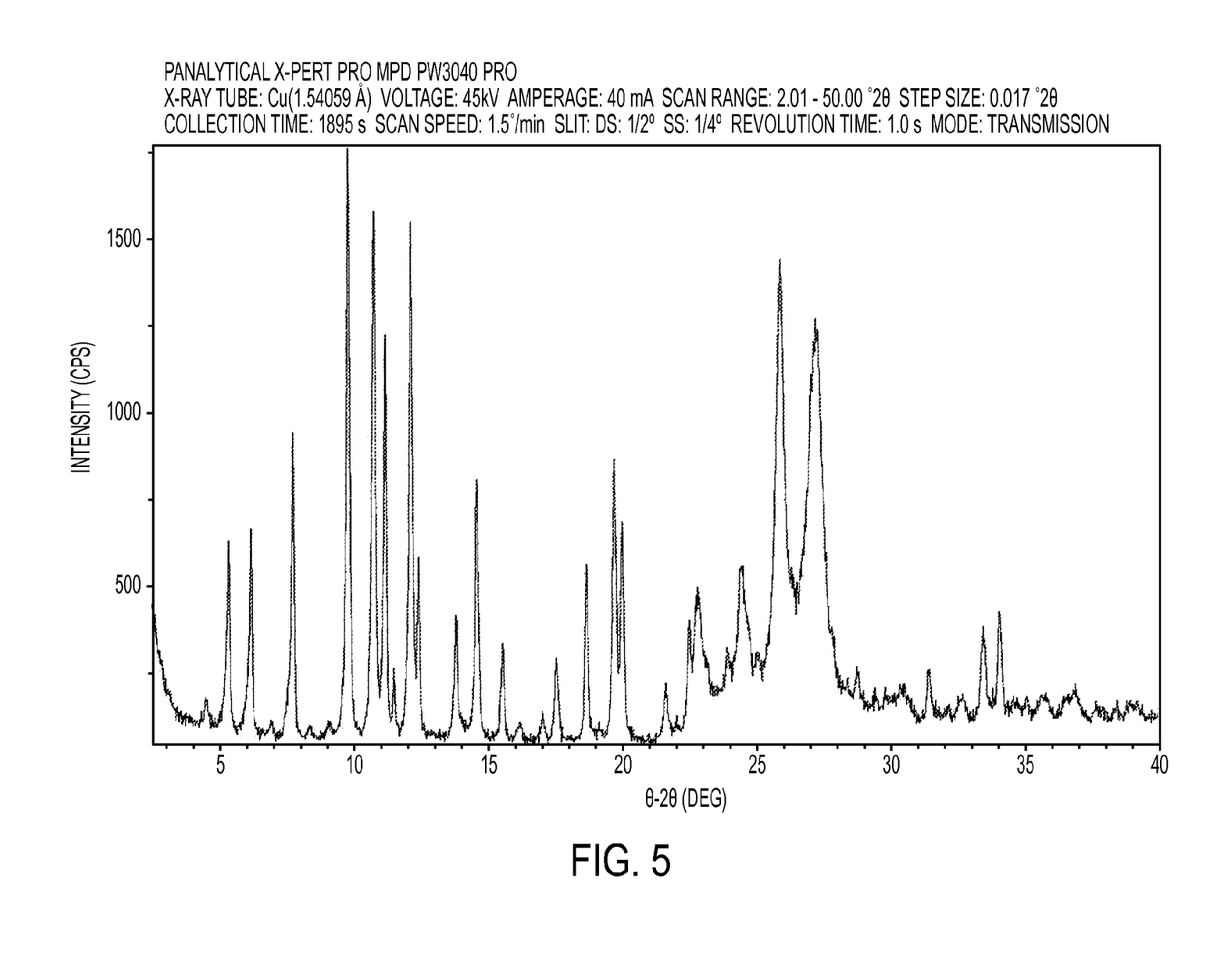
FIG. 5 is an exemplary XRPD pattern of Form E of 5-[3-(2,5-dichloro-4,6-dimethyl-1-oxy-pyridin-3-yl)-[1,2,4]oxadiazol-5-yl]-3-nitrobenzene-1,2-diol, according to one embodiment of the invention.

Polymorph E is a crystalline polymorph and, thus, characterizable by one or more of the peaks of its powder X-ray diffraction pattern (XRPD). The diffraction pattern was recorded with Cu-Kα radiation and is given in the following table.

TABLE 11

XRPD of polymorph E

| Peak Position (°2θ) | Rel. Intensity (%) |
| --- | --- |
| 4.5 | 8 |
| 5.4 | 34 |
| 6.2 | 36 |
| 6.9 | 4 |
| 7.8 | 52 |
| 8.4 | 3 |
| 9.8 | 100 |
| 10.8 | 89 |
| 11.2 | 69 |
| 11.5 | 11 |
| 12.2 | 87 |
| 12.4 | 31 |
| 13.8 | 22 |
| 14.6 | 44 |
| 15.6 | 16 |
| 16.2 | 4 |
| 17.1 | 5 |
| 17.6 | 15 |
| 18.7 | 30 |
| 19.8 | 48 |

TABLE 11-continued

XRPD of polymorph E

| Peak Position (°2θ) | Rel. Intensity (%) |
|---|---|
| 20.1 | 37 |
| 21.7 | 8 |
| 22.6 | 21 |
| 22.9 | 26 |
| 24.0 | 16 |
| 24.5 | 30 |
| 25.1 | 16 |
| 26.0 | 81 |
| 27.3 | 68 |
| 28.8 | 13 |
| 30.6 | 9 |
| 31.5 | 11 |
| 32.7 | 8 |
| 33.5 | 20 |
| 34.1 | 21 |
| 35.8 | 8 |
| 36.9 | 9 |
| 39.2 | 7 |

Preferably, polymorph E is characterized by one or more of the above peaks in the range of from about 5 to about 25°/2θ which is a highly characteristic region of XRPDs. More preferably, polymorph E is characterized by 2 to 10, preferably 3 to 5, peaks within the range of from about 5 to about 25°/2θ. Even more preferably, the polymorph E is characterized by the signals at 7.8, 9.8, 12.2, 15.6, 16.2, 17.6, 19.8, 21.7, 22.9, and 24.5°/2θ. Most preferably, polymorph E is characterized by the signals at 9.8, 11.2, 19.8 and 24.5°/2θ.

Polymorph E may be further characterised by showing an endotherm at 159° C. in a Differential Scanning calorimetry (DSC) thermogram. Polymorph E may be even further characterised by showing an exotherm at 243° C. in a Differential Scanning calorimetry (DSC) thermogram.

Polymorph E is also characterizable by one or more of the following FT-Raman Peak Positions:

TABLE 12

Raman spectra of polymorph E

| Peak position (cm$^{-1}$) | Rel. Intensity (%) |
|---|---|
| 127 | 58 |
| 216 | 16 |
| 231 | 17 |
| 260 | 16 |
| 341 | 21 |
| 384 | 20 |
| 461 | 15 |
| 498 | 20 |
| 526 | 14 |
| 712 | 13 |
| 739 | 26 |
| 769 | 10 |
| 816 | 19 |
| 893 | 15 |
| 922 | 19 |
| 972 | 17 |
| 1005 | 27 |
| 1022 | 45 |
| 1057 | 17 |
| 1174 | 15 |
| 1209 | 23 |
| 1234 | 31 |
| 1269 | 34 |
| 1288 | 33 |
| 1327 | 35 |
| 1356 | 100 |

TABLE 12-continued

Raman spectra of polymorph E

| Peak position (cm$^{-1}$) | Rel. Intensity (%) |
|---|---|
| 1412 | 35 |
| 1460 | 29 |
| 1506 | 31 |
| 1533 | 52 |
| 1556 | 58 |
| 1583 | 97 |
| 1635 | 79 |
| 2931 | 11 |

Preferably, polymorph E is characterizable by one or more, preferably 2 to 6, and more preferably 3 to 5, peak positions in the above table. More preferably, polymorph E is characterized by one or more of the peaks at 127, 1022, 1269, 1288, 1327, 1356, 1412, 1533, 1556, 1583, and 1635 cm$^{-1}$. Most preferably, polymorph E is characterized by the peaks at 1356, 1533, 1556, 1583, and 1635 cm$^{-1}$.

Polymorph E is also characterizable by one or more of the following peak positions in Solid State $^{13}$C-NMR:

TABLE 13

Solid State $^{13}$C-NMR of polymorph E
Peak Positions
(ppm)

| |
|---|
| 175.2 |
| 164.2 |
| 158.8 |
| 151.8 |
| 147.1 |
| 145.5 |
| 143.4 |
| 139.4 |
| 136.4 |
| 133.6 |
| 130.7 |
| 127.3 |
| 124.8 |
| 123.3 |
| 118.1 |
| 108.3 |
| 105.1 |
| 19.4 |
| 17.6 |

Preferably, polymorph E is characterizable by one or more, preferably 2 to 6, and more preferably 3 to 5, peak positions in the above table. Most preferably, polymorph C is characterized by the peaks at 151.8, 133.6, 105.1 and 19.4 ppm.

In yet another embodiment, the present invention relates to a polymorph of the compound of the invention which is, in the following specification, referred to as polymorph F. A process for the preparation of polymorph F is given in the experimental section.

Figure 6:
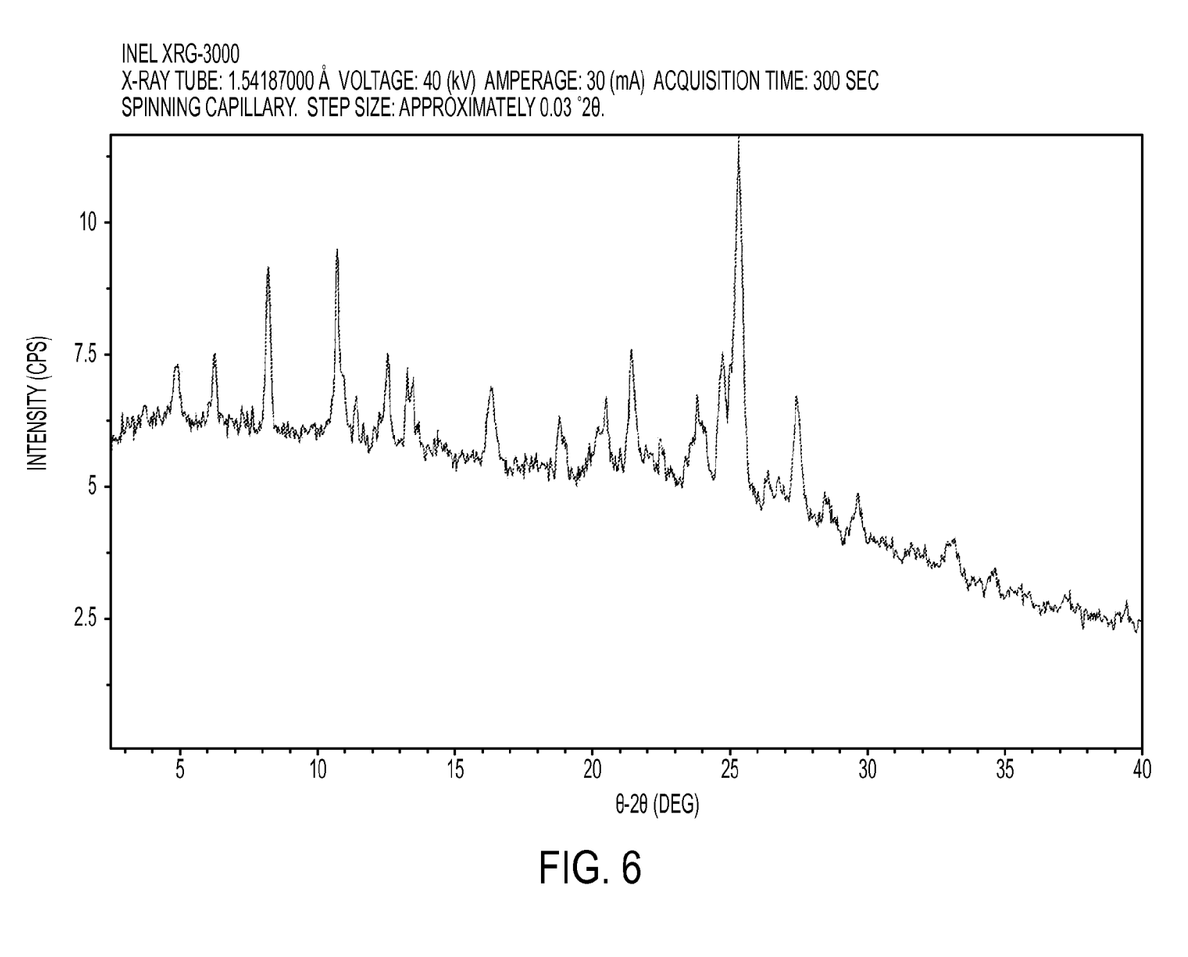
FIG. 6 is an exemplary XRPD pattern of Form F of 5-[3-(2,5-dichloro-4,6-dimethyl-1-oxy-pyridin-3-yl)-[1,2,4]oxadiazol-5-yl]-3-nitrobenzene-1,2-diol, according to one embodiment of the invention.

Polymorph F is a crystalline polymorph and, thus, characterizable by one or more of the peaks of its powder X-ray diffraction pattern (XRPD). The diffraction pattern was recorded with Cu-Kα radiation and is given in the following table.

TABLE 14

XRPD of polymorph F

| Peak Position (°2θ) | Rel. Intensity (%) |
|---|---|
| 4.9 | 62 |
| 6.3 | 64 |
| 8.2 | 80 |
| 10.7 | 81 |
| 11.4 | 58 |
| 12.6 | 65 |
| 13.5 | 59 |
| 14.4 | 49 |
| 16.4 | 58 |
| 18.8 | 55 |
| 20.5 | 56 |
| 21.5 | 66 |
| 23.9 | 58 |
| 24.8 | 65 |
| 25.4 | 100 |
| 26.4 | 46 |
| 27.5 | 57 |
| 28.5 | 42 |
| 29.7 | 42 |
| 33.2 | 33 |
| 34.7 | 28 |

Preferably, polymorph F is characterized by one or more of the above peaks in the range of from about 5 to about 25°/2θ which is a highly characteristic region of XRPDs. More preferably, polymorph F is characterized by 2 to 10, preferably 3 to 5, peaks within the range of from about 5 to about 25°/2θ. Even more preferably, the polymorph F is characterized by the signals at 8.2, 10.7, 12.6, 13.5, 16.4 and 25.4°/2θ. Most preferably, polymorph F is characterized by the signals at 10.7, 12.6, 16.4 and 25.4°/2θ.

In interconversion experiments, it was found that the polymorphs C, D, E, and F convert into polymorph A or B, i.e. modifications A and B are kinetically stable polymorphs. Furthermore, it was found that polymorph B converts into polymorph A when slurried in water containing crystal seeds of modification A over prolonged periods of time. Thus, polymorph A is the thermodynamically stable polymorph.

In particular, drying of polymorph C under vacuum at ambient temperature or at 60° C. produced polymorph B, and drying of polymorph E under vacuum at ambient temperature or at 60° C. produced polymorph A.

Given the fact that modifications A and B are thermodynamically stable and kinetically stable, respectively, they will in particular be characterized by good storage stability. Storage stability of the polymorph is defined herein as a lack of rearrangement of one polymorphic modification into another modification under storage conditions of 60% relative humidity and 25° C. over a period of 3 months. Accordingly, physical parameters related to the polymorphic modification such as the XRPD, Raman spectra and the Differential Scanning Calorimetry (DSC) thermogram will not change upon storage under the above-specified conditions.

Furthermore, these polymorphs will also exhibit stable dissolution properties as these properties are dependent on the above defined storage stability of the polymorph. Accordingly, the modifications A and B are also characterized in that they will not be subject to a change in their dissolution profile upon storage. A lack of change in the dissolution profile is defined herein as a variation of the time period until 80% of the polymorph has dissolved under test conditions according to the USP Paddle Test Method, USP, 30th Edition, The National Formulary 25th Edition, 2007, The United States Pharmacopeial Convention, Rockville, volume 1, chapter 711, of less than 10%, preferably less than 5% and most preferably less than 1%, after storage under conditions of 60% relative humidity at 25° C. over a period of at least 3 months.

The polymorphs of the present invention may be used as active pharmaceutical ingredients in pharmaceutical formulations such as tablets, capsules or injections, without or in combination with one or more pharmaceutically acceptable additives such as sugar, starch, starch derivatives, cellulose, cellulose derivatives, release agents, anti-adhesive agents and agents for regulating flowability.

With regard to pharmaceutical formulations comprising polymorph A the present invention also relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that the X-ray powder diffractogram of the composition exhibits one or more, preferably 1 to 6, more preferably 2 to 4, and most preferably 3, 2θ angles from the following list of 2θ angles: 6.6, 6.9, 11.8, 13.2, 17.2, 17.9, 19.8, 22.6, 23.2, 23.8, 24.3, and 25.3. Preferably, said formulation is characterized by an XRPD having one or more of the following characteristic peaks for polymorph A: 6.6, 23.2 and 24.3.

Furthermore, said pharmaceutical composition may further be characterized in that its Raman spectrum exhibits at least one, preferably 1 to 6, more preferably 2 to 4, and most preferably 3, peaks from the following peak list [cm$^{-1}$]: 145, 170, 216, 237, 256, 285, 339, 370, 420, 442, 465, 505, 526, 710, 810, 974, 1007, 1059, 1159, 1228, 1254, 1277, 1325, 1387, 1414, 1448, 1498, 1537, 1589, 1628, 2927.

Furthermore, said pharmaceutical composition may also be further characterized in that its Solid State 13C-NMR spectrum (100 MHz) exhibits at least one, preferably 1 to 6, more preferably 2 to 4, and most preferably 3, peaks from the following peak list [ppm]: 174.0, 163.9, 150.4, 148.8, 144.5, 140.2, 134.8, 133.2, 129.8, 124.9, 124.0, 122.1, 114.6, 22.5, and 15.7.

The pharmaceutical formulations comprising polymorph A may also exhibit an exotherm at 251° C. in a Differential Scanning calorimetry (DSC) thermogram.

In an alternative embodiment, with regard to pharmaceutical formulations comprising polymorph B, the present invention relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that its X-ray powder diffractogram exhibits one or more, preferably 1 to 6, more preferably 2 to 4, and most preferably 3, 2θ angles from the following list of 2θ angles: 5.7, 6.9, 8.0, 9.8, 11.3, 11.9, 13.8, 14.4, 16.9, 19.6, and 20.4. Preferably, said formulation is characterized by an XRPD having one or more of the following characteristic peaks for polymorph B: 5.7, 16.9 and 19.6.

Furthermore, said pharmaceutical composition may further be characterized in that its Raman spectrum exhibits at least one, preferably 1 to 6, more preferably 2 to 4, and most preferably 3, peaks from the following peak list [cm$^{-1}$]: 141, 214, 235, 253, 280, 339, 361, 372, 399, 415, 440, 463, 505, 526, 710, 812, 887, 926, 970, 1001, 1059, 1157, 1227, 1292, 1317, 1385, 1406, 1444, 1504, 1537, 1583, 1630, and 2933.

Furthermore, said pharmaceutical composition may also be further characterized in that its Solid State $^{13}$C-NMR spectrum (100 MHz) exhibits at least one, preferably 1 to 6, more preferably 2 to 4, and most preferably 3, peaks from the following peak list [ppm]: 174.4, 164.7, 150.3, 139.1, 133.9, 132.8, 123.5, 120.3, 114.0, 112.6, 19.8, and 16.6.

The pharmaceutical formulations comprising polymorph B may also exhibit an exotherm at 237° C., in a Differential Scanning calorimetry (DSC) thermogram.

In an alternative embodiment, with regard to pharmaceutical formulations comprising polymorph C, the present invention relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that its X-ray powder diffractogram exhibits one or more, preferably 1 to 6, more preferably 2 to 4, and most preferably 3, 2θ angles from the following list of 2θ: 4.9, 7.3, 9.5, 9.9, 10.3, 13.3, 13.8, 14.5, 17.2, 18.0, 19.1, 19.9, 20.7, 21.9, 22.6, 23.4, 24.0, 24.6, 24.9, and 25.3. Preferably, said formulation is characterized by an XRPD having one or more of the following characteristic peaks for polymorph C: 7.3, 19.1, 21.9 and 23.4.

Furthermore, said pharmaceutical composition may further be characterized in that its Raman spectrum exhibits at least one, preferably 1 to 6, more preferably 2 to 4, and most preferably 3, peaks from the following peak list [cm$^{-1}$]: 143, 214, 237, 253, 282, 299, 339, 370, 401, 418, 444, 465, 507, 530, 667, 710, 739, 810, 972, 1003, 1061, 1147, 1244, 1281, 1317, 1352, 1387, 1406, 1450, 1483, 1506, 1537, 1585, 1630, and 2918.

Furthermore, said pharmaceutical composition may also be further characterized in that its Solid State 13C-NMR spectrum (100 MHz) exhibits at least one, preferably 1 to 6, more preferably 2 to 4, and most preferably 3, peaks from the following peak list [ppm]: 173.9, 165.0, 150.7, 141.0, 138.6, 133.5, 122.8, 120.3, 114.0, 112.4, 41.1, 20.2, and 17.9.

The pharmaceutical formulations comprising polymorph C may also exhibit an exotherm at 203° C. in a Differential Scanning calorimetry (DSC) thermogram.

In an alternative embodiment, with regard to pharmaceutical formulations comprising polymorph D, the present invention relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that its X-ray powder diffractogram exhibits one or more, preferably 2 to 10, more preferably 3 to 5, and most preferably 4, 2θ angles from the following list of 2θ angles: 11.6, 12.3, 20.0, 20.7, 21.4, 23.8, 24.8, 26.6, 27.4, 28.0, 29.1, 31.1, 32.0, 33.3, 35.0, and 36.0.

In an alternative embodiment, with regard to pharmaceutical formulations comprising polymorph E, the present invention relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that its X-ray powder diffractogram exhibits one or more, preferably 1 to 6, more preferably 2 to 4, and most preferably 3, 2θ angles from the following list of 2θ angles: 4.5, 5.4, 6.2, 6.9, 7.8, 8.4, 9.8, 10.8, 11.2, 11.5, 12.2, 12.4, 13.8, 14.6, 15.6, 16.2, 17.1, 17.6, 18.7, 19.8, 20.1, 21.7, 22.6, 22.9, 24.0, 24.5, 25.1, 26.0, 27.3, 28.8, 30.6, 31.5, 32.7, 33.5, 34.1, 35.8, 36.9, and 39.2. Preferably, said formulation is characterized by an XRPD having one or more of the following characteristic peaks for polymorph E: 7.8, 15.6, 16:2, 17.6, 21.7 and 22.9.

Furthermore, said pharmaceutical composition may further be characterized in that its Raman spectrum exhibits at least one, preferably 1 to 6, more preferably 2 to 4, and most preferably 3, peaks from the following peak list [cm$^{-1}$]: 127, 216, 231, 260, 341, 384, 461, 498, 526, 712, 739, 769, 816, 893, 922, 972, 1005, 1022, 1057, 1174, 1209, 1234, 1269, 1288, 1327, 1356, 1412, 1460, 1506, 1533, 1556, 1583, 1635, and 2931.

Furthermore, said pharmaceutical composition may also be further characterized in that its Solid State $^{13}$C-NMR spectrum (100 MHz) exhibits at least one, preferably 2 to 10, more preferably 3 to 5, and most preferably 4, peaks from the following peak list [ppm]: 175.2, 164.2, 158.8, 151.8, 147.1, 145.5, 143.4, 139.4, 136.4, 133.6, 130.7, 127.3, 124.8, 123.3, 118.1, 108.3, 105.1, 19.4, and 17.6.

The pharmaceutical formulations comprising polymorph E may also exhibit an exotherm at 243° C. in a Differential Scanning calorimetry (DSC) thermogram.

In an alternative embodiment, with regard to pharmaceutical formulations comprising polymorph F, the present invention relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that its X-ray powder diffractogram exhibits one or more, preferably 2 to 10, more preferably 3 to 5, and most preferably 4, 2θ angles from the following list of 2θ angles: 4.9, 6.3, 8.2, 10.7, 11.4, 12.6, 13.5, 14.4, 16.4, 18.8, 20.5, 21.5, 23.9, 24.8, 25.4, 26.4, 27.5, 28.5, 29.7, 33.2, and 34.7. Preferably, said formulation is characterized by an XRPD having one or more of the following characteristic peaks for polymorph F: 8.2, 12.6, 13.5, and 16.4.

When properly formulated by the skilled person, the physical properties of the polymorphs are reflected in the pharmaceutical formulations. Accordingly, pharmaceutical formulations comprising the stable polymorphs A and/or B will also be storage stable. Thus, pharmaceutical formulations containing modifications A and/or B are further characterized in that they will not be subject to a change in their dissolution profile upon storage. A lack of change in the dissolution profile is defined herein as a lack of variation of the time period until 80% of the active pharmaceutical ingredient has been released under test conditions according to the USP Paddle Test Method, USP, 30th Edition, The National Formulary 25th Edition, 2007, The United States Pharmacopeial Convention, Rockville, volume 1, chapter 711, of less than 10%, preferably less than 5% and most preferably less than 1%, after storage under conditions of 60% relative humidity at 25° C. over a period of at least 3 months.

Furthermore, the stability of modifications A and B can be used to convert metastable modifications such as modifications C to F into the more stable modifications A or B. Likewise, due to the stability of modifications A and B, mixtures of metastable modifications can be converted to polymorphically pure modifications A and B e.g. by seeding slurries of such mixtures with modification A or B. Modification B can also be converted to modification A e.g. by seeding a slurry of modification B with seeding crystals of modification A.

It is particularly preferred to convert modifications less stable than modification A such as amorphic, metastable and polymorphically impure modifications to the thermodynamically most stable modification A. The most preferred process for doing so is seeding such modifications or mixtures of modifications with seeding crystals of modification A. Another preferred process for achieving a conversion is the dissolution of said modifications, followed by seeding with crystals of modification A.

Experimental Section:

Process for the Preparation of Polymorph A:

A 1600 L reactor was charged with 245 kg formic acid and 10 kg 5-[3-(2,5-dichloro-4,6-dimethyl-1-oxy-pyridin-3-yl)-[1,2,4]oxadiazol-5-yl]-3-nitrobenzene-1,2-diol. The mixture was heated to 70-75° C. until the solid dissolved. The hot solution was then filtered to a 250 L reactor, and then cooled to 25-35° C. Vacuum was applied and the mixture was distilled at 50° C. until 50-70 liters remained. To this mixture 160 kg isopropanol was introduced. The mixture was cooled to 5-10° C. and was allowed to stir for 10 hours. The suspension was then centrifuged and washed with 13 kg isopropanol. The wet material was removed from the centrifuge and dried in a vacuum tray drier. The dried material weight was 8.995 kg after sampling. The yield of polymorph A was 9.395 kg, 93.9%.

Process for the Preparation of Polymorph B:

161.6 mg of 5-[3-(2,5-dichloro-4,6-dimethyl-1-oxy-pyridin-3-yl)-[1,2,4]oxadiazol-5-yl]-3-nitrobenzene-1,2-diol were added to a glass vial. Formic acid (2.0 mL) was added and the sample warmed to 73° C. in an oil bath. The resulting mixture was filtered though a 0.2 µm nylon filter into a clean vial at room temperature. Solids of polymorph B were precipitated via addition of water (2.0 mL) and were collected by filtration.

Process for the Preparation of Polymorph C:

161.0 mg of 5-[3-(2,5-dichloro-4,6-dimethyl-1-oxy-pyridin-3-yl)-[1,2,4]oxadiazol-5-yl]-3-nitrobenzene-1,2-diol were added to a glass vial and dissolved in DMSO (4.0 mL). The solution was filtered through a 0.2 µm nylon filter into a clean vial and evaporated to dryness in a centrifugal evaporator set at 50° C. under vacuum to yield polymorph C.

Process for the Preparation of Polymorph D:

A saturated solution of 5-[3-(2,5-dichloro-4,6-dimethyl-1-oxy-pyridin-3-yl)-[1,2,4]oxadiazol-5-yl]-3-nitrobenzene-1,2-diol was generated in a 1:1 dioxane:water mixture (1.0 mL). The resulting mixture was filtered through a 0.2 µm nylon filter into a clean vial and evaporated to dryness under ambient conditions to yield polymorph D.

Process for the Preparation of Polymorph E:

151.2 mg of 5-[3-(2,5-dichloro-4,6-dimethyl-1-oxy-pyridin-3-yl)-[1,2,4]oxadiazol-5-yl]-3-nitrobenzene-1,2-diol were added to a glass vial and dissolved in pyridine (3.0 mL). The solution was filtered through a 0.2 µm nylon filter into a clean vial and evaporated to dryness under a nitrogen stream yielding polymorph E.

Process for the Preparation of Polymorph F:

A saturated solution of 5-[3-(2,5-dichloro-4,6-dimethyl-1-oxy-pyridin-3-yl)-[1,2,4]oxadiazol-5-yl]-3-nitrobenzene-1,2-diol was generated in DMSO (0.500 mL). The resulting mixture was filtered through a 0.2 µm nylon filter into a clean vial. Approximately 60 µL of this solution was dispensed into a capillary. The capillary was placed into a centrifugal evaporator at ambient temperature and the solvent removed under reduced pressure yielding polymorph F.

Analysis was performed with the following instrumentation:

1. PANalytical X'Pert Pro Diffractometer

Samples of polymorphs A, C and E were analyzed using a PANalytical X'Pert Pro diffractometer. The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. A beam-stop and helium were used to minimize the background generated by air scattering. Soller slits were used for the incident and diffracted beams to minimize axial divergence. Diffraction patterns were collected using a scanning position-sensitive detector (X'Celerator) located 240 mm from the specimen. The data-acquisition parameters of each diffraction pattern are displayed above the image of each pattern in appendix data section. Prior to the analysis a silicon specimen (NIST standard reference material 640c) was analyzed to verify the position of the silicon 111 peak.

2. Shimadzu XRD-6000 Diffractometer

Samples of polymorph B were analyzed using a Shimadzu XRD-6000 X-ray powder diffractometer using Cu Kα radiation. The instrument is equipped with a long fine focus X-ray tube. The tube voltage and amperage were set at 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40° 2θ was used. A silicon standard was analyzed to check the instrument alignment. Samples were prepared for analysis by placing them in an aluminum/silicon sample holder.

3. Bruker D8 Discover Diffractometer

Samples of polymorph D were analyzed using a Bruker D-8 Discover diffractometer and Bruker's General Area Diffraction Detection System (GADDS, v. 4.1.20). An incident beam of CuKα radiation was produced using a fine-focus tube (40 kV, 40 mA), a Gael mirror, and a 0.5 mm double-pinhole collimator. The sample was packed between 3-micron thick films to form a portable disc-shaped specimen and analyzed using a transmission geometry. The incident beam was scanned and rastered over the sample during the analysis to optimize orientation statistics. A beam-stop was used to minimize air scatter from the incident beam at low angles. Diffraction patterns were collected using a Hi-Star area detector located 15 cm from the sample and processed using GADDS. The intensity in the GADDS image of the diffraction pattern was integrated using a step size of 0.04° 2θ. The integrated patterns display diffraction intensity as a function of 2θ. Prior to the analysis a silicon standard was analyzed to verify the Si 111 peak position.

4. Inel XRG-3000 Diffractometer

X-ray powder diffraction (XRPD) analyses of polymorph F were performed using an Inel XRG-3000 diffractometer equipped with a CPS (Curved Position Sensitive) detector with a 2q range of 120°. Real time data were collected using Cu-Kα radiation. The tube voltage and amperage were set to 40 kV and 30 mA, respectively. The monochromator slit was set at 1-5 mm by 160 µm. The patterns are displayed from 2.5-40° 2q. Samples were prepared for analysis by packing them into thin-walled glass capillaries. Each capillary was mounted onto a goniometer head that is motorized to permit spinning of the capillary during data acquisition. The samples were analyzed for 300 seconds. Instrument calibration was performed using a silicon reference standard.

DSC for polymorph A was performed using TA Instruments model Q2000 calorimeter. The samples were placed in an aluminium DSC pan, the weight accurately recorded and the pan crimped. The sample cell was equilibrated at 25° C. and heated under nitrogen purge at a rate of 10° C./min up to a final temperature of 250 or 300° C. Indium metal was used as calibration standard. For all other polymorphs analyses were performed using TA Instruments model 2920 calorimeter. The sample cell was equilibrated at 25° C. and heated under nitrogen purge at a rate of 10° C./min up to a final temperature of 250 or 300° C. Indium metal was used as calibration standard.

TGA analyses were performed on a TA Instruments model 2950 thermogravimetric analyzer. The furnace was equilibrated at 25° C. and heated under nitrogen purge at a rate of 10° C./min up to a final temperature of 300 or 350° C. Nickel and Alume™ were used as calibration standards.

Hotstage microscopy was performed using a Linkam hotstage (model FTIR 600) mounted to a Leica DMLP microscope. Samples were observed using crossed polarized light. Samples were sandwiched between coverslips and visually observed as the stage was heated. The hotstage was calibrated using USP melting point standards. FT-Raman spectra were acquired on an FT-Raman 960 spectrometer (Thermo Nicolet) using an excitation wavelength of 1064 nm. Approximately 0.2-0.3 W of Nd:YVO$_4$ laser power was used to irradiate the samples. The Raman spectra were measured with a germanium detector. The samples were prepared for analysis by placing the material in a glass tube and positioning the tube in a gold-coated tube holder in the accessory. A total of 256 sample scans were collected from 3600-100 cm$^{-1}$ at a spectral resolution of 4 cm$^{-1}$, using Happ-Genzel apodization. Wavelength calibration was performed using sulfur and cyclohexane.

For $^{13}$C-ss MAS NMR spectroscopy, samples were prepared by packing them into 4 mm PENCIL type zirconia rotors. Acquisition was performed on INOVA-400 at ambient temperature using VNMR6.1C (patch a11205) as processing software. The acquisition parameters were as follows:

Sequence: xpolytlrhol
Relax. Delay: 40.000 sec
Pulse width: 2.2 usec (90.0 deg.) or 2.2 usec (76.2 deg) for polymorph E
Acq. Time: 0.030 sec
Spectral width: 44994.4 Hz (447.517 ppm)
400 scans
2 dummy scans
Acquired points: 2700
Observed Nucleus: C13 (100 MHz)
Decoupled Nucleus: H1 (400 MHz)
SPINAL-64 decoupling
Cross Polarization
Tangent RAMP-CP on C13
Contact time: 5.0 ms
Spinning rate: 12000 Hz

The invention claimed is:

1. A crystal form of 5-[3-(2,5-dichloro-4,6-dimethyl-1-oxy-pyridin-3-yl)-[1,2,4]oxadiazol-5-yl]-3-nitrobenzene-1,2-diol, having an X-ray powder diffractogram that exhibits peaks at about the following 2θ angles: 5.7, 6.9, 13.8 and 19.6.

2. The crystal form of 5-[3-(2,5-dichloro-4,6-dimethyl-1-oxy-pyridin-3-yl)-[1,2,4]oxadiazol-5-yl]-3-nitrobenzene-1,2-diol according to claim 1, wherein the X-ray powder diffractogram exhibits additional peaks at about the following 2θ angles: 11.9, and 16.9.

3. The crystal form of 5-[3-(2,5-dichloro-4,6-dimethyl-1-oxy-pyridin-3-yl)-[1,2,4]oxadiazol-5-yl]-3-nitrobenzene-1,2-diol according to claim 1, having a Raman spectrum with peaks at about 505, 1292, 1385, 1583, and 1630 cm$^{-1}$.

4. The crystal form of 5-[3-(2,5-dichloro-4,6-dimethyl-1-oxy-pyridin-3-yl)-[1,2,4]oxadiazol-5-yl]-3-nitrobenzene-1,2-diol according to claim 1, having a Solid State $^{13}$C-NMR spectrum that exhibits peaks at about 150.3, 133.9, 112.6 and 19.8 ppm.

5. The crystal form of 5-[3-(2,5-dichloro-4,6-dimethyl-1-oxy-pyridin-3-yl)-[1,2,4]oxadiazol-5-yl]-3-nitrobenzene-1,2-diol according to claim 1, having a Differential Scanning calorimetry (DSC) thermogram that exhibits an exotherm at about 237° C.

* * * * *